United States Patent [19]
Weiss

[11] Patent Number: 5,751,125
[45] Date of Patent: May 12, 1998

[54] ARTIFICIAL HEART WITH SENSORLESS MOTOR

[75] Inventor: William J. Weiss, Mechanicsburg, Pa.

[73] Assignee: The Penn State Research Foundation, University Park, Pa.

[21] Appl. No.: 555,161

[22] Filed: Nov. 8, 1995

[51] Int. Cl.$^6$ .................................................. H02P 1/00
[52] U.S. Cl. .................. 318/280; 318/290; 318/254; 318/439; 318/138
[58] Field of Search ........................... 318/280, 290, 318/254, 439, 138

[56] References Cited

U.S. PATENT DOCUMENTS

| | | | |
|---|---|---|---|
| 4,162,435 | 7/1979 | Wright | 318/138 |
| 4,446,406 | 5/1984 | Uzuka | 318/254 |
| 4,495,450 | 1/1985 | Tokizaki et al. | 318/138 |
| 4,532,459 | 7/1985 | Erdman et al. | 318/138 |
| 4,678,973 | 7/1987 | Elliott et al. | 318/254 |
| 4,874,993 | 10/1989 | Tanaka et al. | 318/254 |
| 4,970,445 | 11/1990 | Kimura et al. | 318/254 |
| 5,019,756 | 5/1991 | Schwarz | 318/254 |
| 5,028,852 | 7/1991 | Dunfield | 318/254 |
| 5,130,620 | 7/1992 | Inaji et al. | 318/254 |
| 5,134,349 | 7/1992 | Kruse | 318/254 |
| 5,144,209 | 9/1992 | Ingji et al. | 318/254 |
| 5,159,246 | 10/1992 | Ueki | 318/254 |
| 5,177,416 | 1/1993 | Inaji et al. | 318/254 |
| 5,206,567 | 4/1993 | Sakurai et al. | 312/254 |
| 5,254,914 | 10/1993 | Dunfield et al. | 318/254 |
| 5,254,918 | 10/1993 | Ueki | 318/466 |
| 5,291,115 | 3/1994 | Ehsani | 318/701 |
| 5,304,902 | 4/1994 | Ueki | 318/254 |
| 5,311,105 | 5/1994 | Nakai et al. | 318/254 |
| 5,339,013 | 8/1994 | Nakai et al. | 318/254 |
| 5,350,984 | 9/1994 | Carobolante et al. | 318/254 |
| 5,363,032 | 11/1994 | Hanson et al. | 322/10 |
| 5,367,233 | 11/1994 | Maeda | 318/254 |
| 5,384,527 | 1/1995 | Rozman et al. | 322/10 |
| 5,428,275 | 6/1995 | Carr et al. | 318/146 |
| 5,430,362 | 7/1995 | Carr et al. | 318/779 |
| 5,489,810 | 2/1996 | Ferreira et al. | 310/54 |
| 5,493,195 | 2/1996 | Heglund et al. | 318/701 |

OTHER PUBLICATIONS

Ehsani et al., "Direct Control Strategies Based on Sensing Inductance in Switched Reluctance Motors", 1993 IEEE Bulletin, pp. 10–16.

Feucht, Dennis L., "Sensorless Start-Up Positioning of Brushless Motors", PCIM Mar. 1993, pp. 24–27.

Furuhashi et al., "A Position–and Velocity Sensorless Control for Brushless DC Motors Using an Adaptive Sliding Mode Observer", IEEE Transactions on Industrial Electronics, vol. 39, No. 2, Apr. 1992, pp. 89–95.

Lau Siu–Wo, "An Experimental Study in Sensorless Commutation of the Penn State Artificial Heart", The Pennsylvania State University, Dec. 1990.

Lau et al., "Sensorless Position Control of a Brushless Motor in Circulatory Assist Devices", Mechatronics vol. 1, No. 3, pp. 277–292, 1991.

(List continued on next page.)

*Primary Examiner*—Karen Masih
*Attorney, Agent, or Firm*—Marshall, O'Toole, Gerstein, Murray & Borun

[57] ABSTRACT

An artificial heart assembly, designed for implantation into a subject, which may be a total artificial heart or a ventricular assist device. The artificial heart assembly has a blood inlet conduit, a blood outlet conduit, a pumping mechanism for pumping blood from the blood inlet conduit to the blood outlet conduit, and a sensorless, DC brushless motor operatively connected to the pumping mechanism. The motor is reversibly driven in a first direction and a second direction, the motor changing between the first and second directions at a rate of at least 30 times per minute. The artificial heart assembly has means for periodically applying electrical signals to a plurality of the motor terminals while leaving at least one of the motor terminals unenergized, means for detecting a voltage at the unenergized motor terminal, and means for determining, based upon the voltage at the unenergized terminal, the angular position of the rotor with respect to the stator.

37 Claims, 10 Drawing Sheets

OTHER PUBLICATIONS

Matsui et al., "Brushless dc Motor Control without Position and Speed Sensors", IEEE Transactions on Industry Applications, vol. 28, No., Jan./Feb. 1992, pp. 120–127.

Mosley J. D., Technical Editor, "Spin chips whirl into nondrive applications", EDN–Technology Update, 5 pages.

Ogasawara et al., "An Approach to Position Sensorless Drive for Brushless dc Motors", IEEE Transactions on Industry Applications, vol. 27, No. 5, Sep./Oct. 1991, pp. 928–993.

Ogasawara et al., "A Sensorless Brushless DC Motor System", Electrical Engineering in Japan, vol. 12, No. 5, 1992, pp. 109–118.

Pae, Jr., et al., "Ventricular assist devices for postcardiotomy cardiogenic shock", The Journal of Thoracic and Cardiovascular Surgery, vol. 104, No. 3, Sep. 1992, pp. 541–553.

Panda et al., "Waveform detection technique for indirect rotor–position sensing of switched–reluctance motor drives", IEE Proceedings–B, vol. 140, No. 1, Jan. 1993, pp. 80–88.

Peters et al., "ICs provide control for sensorless dc motors", EDN–Design Feature, Apr. 29, 1993, pp. 85–94.

Pierce et al., "A long–term ventricular assist system", The Journal of Thoracic and Cardiovascular Surgery, vol. 105, No. 3, pp. 520–524, Mar. 1993.

Poirier et al., "An Ambulatory, Intermediate Term Left Ventricular Assist Device", vol. XXXV Trans Am Soc Artif Intern Organs 1989, pp. 452–455.

Rintoul et al., "Continuing Development of the Cleveland Clinic–Nimbus Total Artificial Heart", ASAIO Journal 1993, pp. M168–M171.

Rosenberg et al., "In Vivo Testing of a Clinical–size Totally Implantable Artificial Heart", Assisted Circulation 4, pp. 236–248, 1995.

Snyder et al., "Indirect Estimation of Circulatory Pressures For Control of an Electric Motor Driven Total Artificial Heart", pp. 87–88, 1985.

Snyder et al., "In Vivo Testing of a Completely Implanted Total Artificial Heart System", ASAIO Journal 1993, pp. M177–M184.

Snyder et al., "Microcomputer Control of Permanently Implanted Blood Pumps", Proceedings of the Second Annual IEEE Symposium on Computer–Based Medical Systems, Minneapolis, Minnesota, Jun. 26–27, 1989, pp. 154–157.

Tatsumi et al., "A Blood Pump with an Interatrial Shunt for Use as an Electrohydraulic Total Artificial Heart", ASAIO Journal 1992, pp. M425–M430.

Weiss et al., "Progress Toward a Completely Implantable Left Ventricular Assist Device at the Pennsylvania State University", Assisted Circulation 4, pp. 124–137, 1995.

Yu et al., "A Compact and Noise Free Electrohydraulic Total Artificial Heart", ASAIO Journal 1993, pp. M386–M391.

The Institute of Electrical and Electronics Engineers Inc., Case Studies in Medical Instrument Design, "Development Of A Totally Implantable Artificial Heart Concept To Implementation", pp. 95–111, 1992.

The Institute of Electrical and Electronics Engineers Inc. Computer Society Press Reprint article, "Microcomputer Control of Permanently Implanted Blood Pumps", pp. 154–157, 1989.

Snyder, A Thesis in Bioengineering, "Automatic Electronic Control of an Electric Motor–Driven Total Artificial Heart", The Pennsylvania State University, The Graduate School, Bioengineering Program, Table of Contents and pp. 1–166, 1987.

| Sector CCW → | 1 | 2 | 3 | 4 | 5 | 6 |
|---|---|---|---|---|---|---|
| Energization table for CCW rotation  A | + | + |   | − | − |   |
| B |   | − | − |   | + | + |
| C | − |   | + | + |   | − |
FIG. 6A
| Sector | 1 | 2 | 3 | 4 | 5 | 6 |
|---|---|---|---|---|---|---|
| Energization table for CW rotation  A | − | − |   | + | + |   |
| B |   | + | + |   | − | − |
| C | + |   | − | − |   | + |
FIG. 6B
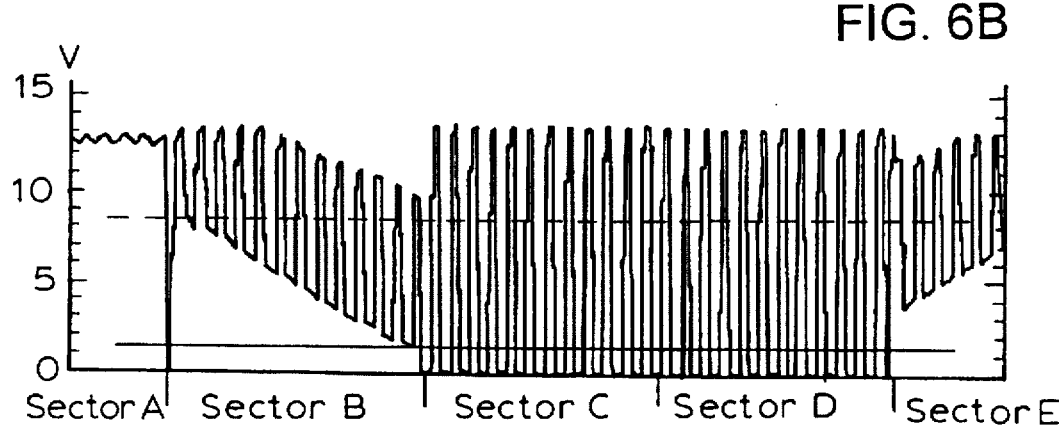
FIG. 7
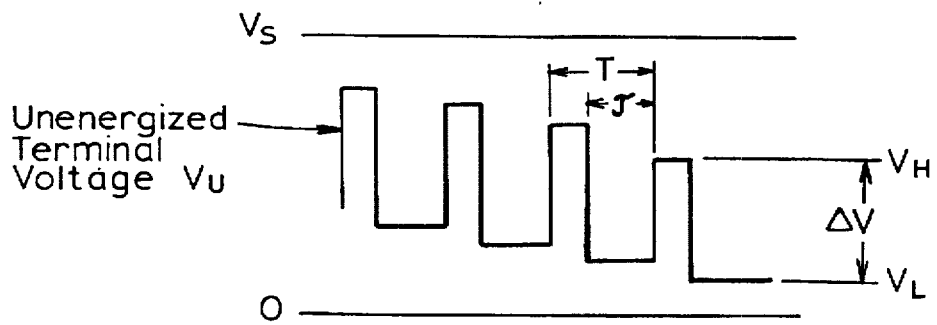
FIG. 8

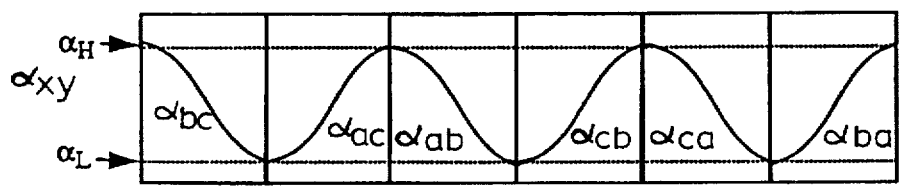
FIG. 11A
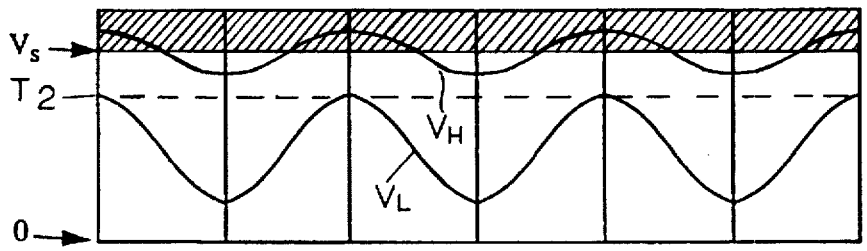
FIG. 11B
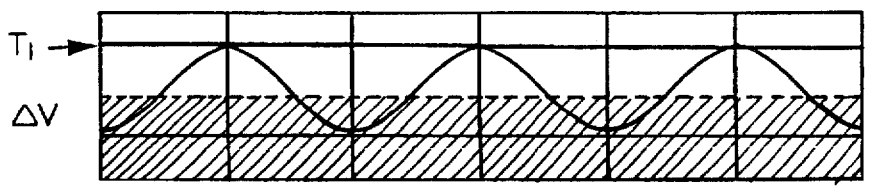
FIG. 11C
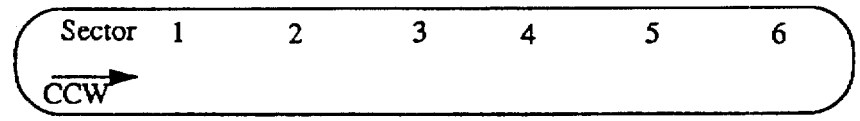
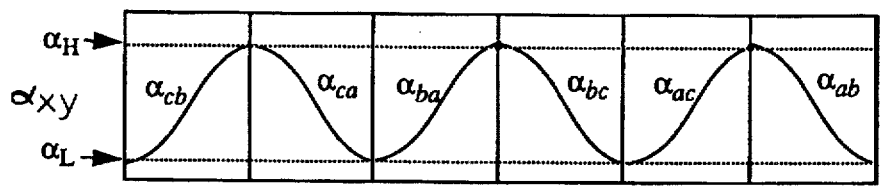
FIG. 12A
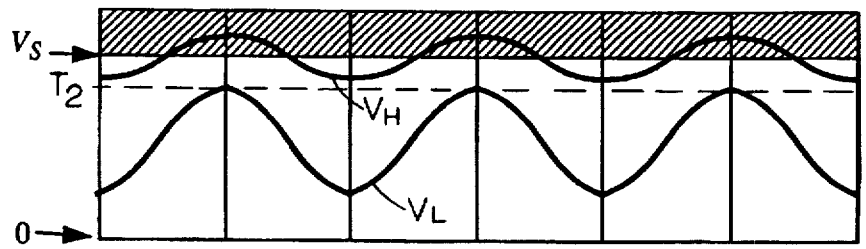
FIG. 12B
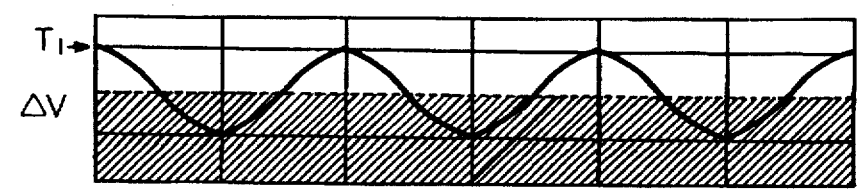
FIG. 12C
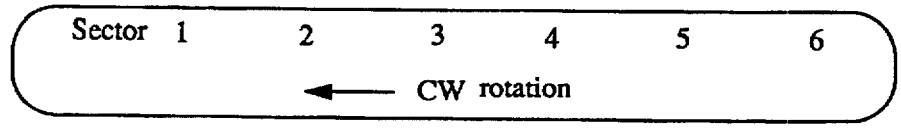

ARTIFICIAL HEART WITH SENSORLESS MOTOR

This patent is subject to Government Contract No. N01-HV-38130 with the National Heart, Lung and Blood Institute.

BACKGROUND OF THE INVENTION

The present invention is directed to an artificial heart assembly with a DC brushless motor which utilizes sensorless positioning to determine the angular position of the rotor with respect to the stator.

An artificial heart assembly intended for use with a subject, such as an animal or human, may be a total artificial heart (TAH) intended to replace the entire heart of the subject, a ventricular assist device (VAD) intended to replace a portion of the subject's heart, or an external blood pump to be used with the subject.

A conventional artificial heart has previously been provided with a DC motor to drive a pumping mechanism for pumping blood through the artificial heart. The DC motor has been provided with a stator and a permanent magnet rotor rotatable with respect to the stator, the rotor being connected to a coupler for translating the rotation of the rotor into linear movement of the blood pumping mechanism.

When starting such a DC motor, it is advantageous to know the angular position of the rotor with respect to the stator so that the windings of the stator can be provided with an appropriate set of excitation signals. It is also advantageous to know the angular position of the rotor when the motor is being driven so that commutation signals can be given at optimal times. In the context of an artificial heart, the position of the rotor has been determined by utilizing sensors, such as Hall sensors. However, incorporating sensors into an artificial heart has a number of disadvantages.

For applications other than artificial hearts, it has been proposed to utilize sensorless detection of the rotor position. In this approach, some type of position-detecting method is used initially, and then when the rotor reaches a threshold speed, the rotor position is detected based on the back-EMF signal generated in the motor. The back-EMF signal cannot be used to detect the rotor position at relatively low rotor speeds since its magnitude is proportional to rotor speed, and at low rotor speeds the magnitude of the back-EMF signal is not large enough for reliable detection.

SUMMARY OF THE INVENTION

The present invention is directed to an artificial heart assembly, designed for implantation into a subject, which may be a total artificial heart or a ventricular assist device. The artificial heart assembly has a blood inlet conduit, a blood outlet conduit, a pumping mechanism for pumping blood from the blood inlet conduit to the blood outlet conduit, and a sensorless, DC brushless motor operatively connected to the pumping mechanism. The motor is reversibly driven in a first direction and a second direction, the motor changing between the first and second directions at a rate of at least 30 times per minute. The motor has a permanent magnet rotor, a stator rotatable relative to the permanent magnet rotor and having a plurality of electrically energizable windings, and a plurality of motor terminals to which the windings are electrically connected.

In one aspect of the invention, the rotor may be in Y possible angular position sectors with respect to the stator, wherein Y has a numeric value greater than two, and the artificial heart assembly has means for periodically applying electrical signals to a plurality of the motor terminals while leaving at least one of the motor terminals unenergized to cause the rotor to rotate alternately in the first direction and second directions, the rotor changing between the first and second directions at a rate of at least about 30 times per minute. The artificial heart assembly includes means for detecting a voltage at the unenergized motor terminal and means for determining, based upon the voltage detected by the detecting means, that the rotor is in one of X possible angular position sectors, where X has a numeric value less than the numeric value of Y.

The detecting means may detect the voltage on the unenergized motor terminal while the rotor is stationary with respect to the stator, and the means for applying electrical signals to the motor terminals may include means for determining when a new set of electrical signals should be applied to the windings, based upon the detection of the voltage at the unenergized motor terminal, in order to move the rotor from a first of the angular position sectors to a second one of the angular position sectors.

The means for determining that the rotor is in one of X possible angular position sectors may include means for determining an inductance ratio based on the voltage on the unenergized terminal and means for comparing the inductance ratio with a threshold value.

In another aspect of the invention, the artificial heart assembly may be provided with means for determining when a new set of electrical signals should be applied to the windings, based upon the detection of the voltage at the unenergized motor terminal, in order to move the rotor from the first angular position sector to the second angular position sector.

The means for applying electrical signals may apply a pulse-width modulated signal to at least one of the motor terminals so that the voltage at the unenergized motor terminal has a plurality of relatively high voltage portions $V_H$ alternated with a plurality of relatively low voltage portions $V_L$, and the determining means may determine when a new set of electrical signals should be applied to the windings based upon one of the voltage portions $V_L$.

The means for determining when a new set of electrical signals should be applied to the windings may comprise means for determining when one of the voltage portions $V_L$ reaches a threshold value, and the artificial heart assembly may include means for calculating a voltage difference $\Delta V$ between one of the voltage portions $V_H$ and one of the voltage portions $V_L$ and means for determining when a new set of electrical signals should be applied to the windings based upon when the voltage difference $\Delta V$ reaches a threshold value.

The invention is also directed to a method of operating an artificial heart assembly having a blood inlet conduit, a blood outlet conduit, a pumping mechanism for pumping blood from the blood inlet conduit to the blood outlet conduit, and a sensorless DC brushless motor coupled to the pumping mechanism and having a permanent magnet rotor, a stator rotatable relative to the rotor and having a plurality of electrically energizable windings and a plurality of motor terminals to which the windings are electrically connected, the rotor being movable from a first angular position sector relative to the stator to a second angular position sector relative to the stator. The method includes the steps of: (a) periodically applying electrical signals to a plurality of the motor terminals while the rotor is moving relative to the stator and while leaving at least one of the motor terminals unenergized, (b) detecting a voltage at the unenergized motor terminal at least about five times while the rotor is in one of the angular position sectors; and (c) determining when a new set of electrical signals should be applied to the windings, based upon the detection of a voltage on the unenergized motor terminal during said step (b), in order to move the rotor from the first angular position sector to the second angular position sector.

These and other features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIGS. 6A and 6B are energization tables for the DC motor of FIG. 1;

FIG. 7 illustrates the voltage on one of the motor windings of the DC motor;

FIG. 8 is a simplified waveform diagram of the voltage on one of the motor windings;

FIGS. 10–12 illustrate various waveforms related to the operation of the DC motor;

DETAILED DESCRIPTION OF A PREFERRED EMBODIMENT

Figure 1:
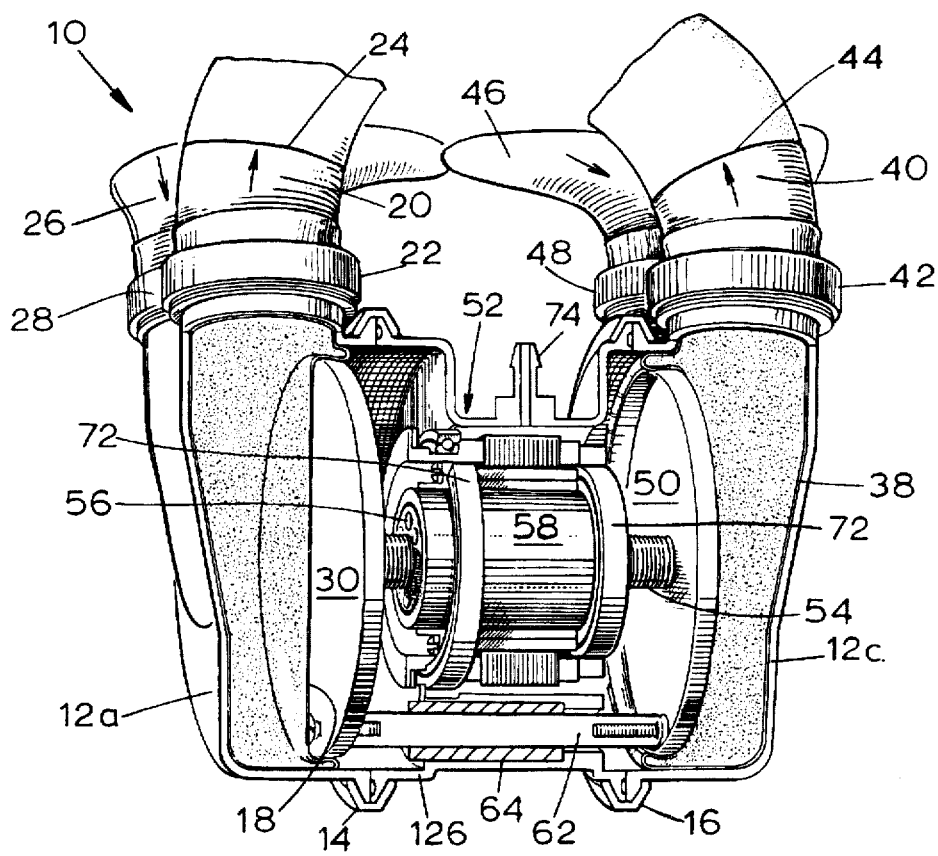
FIG. 1 is a perspective view of a preferred embodiment of an artificial heart in accordance with the invention, portions of which are shown in cross section.

A preferred embodiment of an artificial heart assembly in accordance with the invention is shown as an artificial heart 10 intended to be completely implanted within a subject, such as a human or an animal, and to take the place of the subject's natural heart is illustrated in FIG. 1. The artificial heart 10 has a housing 12 composed of three sections 12a, 12b, 12c which are held together by a pair of annular V-rings 14, 16.

A blood reservoir within a sac 18 disposed within the housing section 12a is fluidly coupled to a blood outlet defined by an artificial vascular graft 20 connected to the housing section 12a via a threaded connector 22. The graft 20 is connected to the pulmonary artery of the subject via a suture line 24. The blood reservoir 18 is fluidly coupled to a blood inlet chamber defined by an artificial graft 26 which is connected to the housing section 12a via a threaded connector 28 and to the right atrium of the subject via a suture line (not shown). A pair of one-way check valves (not shown) are disposed in the blood inlet 26 and the blood outlet 20 to ensure that blood is pumped in the direction shown by the arrows in FIG. 1. A pump mechanism in the form of a pusher plate 30 makes contact with and periodically deforms the blood sac 18 to force blood from the blood inlet 26 to the blood outlet 20.

A blood sac 38 disposed within the housing section 12c is fluidly coupled to a blood outlet defined by an artificial graft 40 connected to the housing section 12c via a threaded connector 42. The graft 40 is connected to the aorta of the subject via a suture line 44. The blood reservoir 38 is coupled to a blood inlet chamber defined by an artificial graft 46 which is connected to the housing section 12c via a threaded connector 48 and to the left atrium of the subject via a suture line (not shown). A pair of one-way check valves (not shown) are disposed in the blood inlet 46 and the blood outlet 40 to ensure that blood is pumped in the direction shown by the arrows. A pusher plate 50 makes contact with and periodically deforms the blood sac 38 to force blood from the blood inlet 46 to the blood outlet 40.

The pusher plates 30, 50 are driven laterally back and forth by a DC brushless motor 52 coupled to the pusher plates 30, 50 via a drive screw 54 and a coupling mechanism composed of a plurality of threaded elongate rollers 56 disposed within a cylindrical nut 58 fixed to a rotor 60 of the motor 52. Rotation of the rotor 60 causes the nut 58 and rollers 56 to rotate, thus causing the drive screw 54 to be linearly displaced in a direction parallel to its longitudinal central axis. A guide rod 62 is connected between the two pusher plates 30, 50 and passes through a fixed bushing 64 to prevent the plates 30, 50 from rotating. Other mechanisms for coupling the rotor 60 to the drive screw 54 could be used.

The rotation of the rotor 60 is controlled via the electrical energization of a plurality of windings 68 of a stator 70 (FIG. 2) which is rotatably coupled to the rotor 60 via a pair of cylindrical bearings 72. A wire port 74 is formed in the housing section 12b to allow the passage of wires from the windings 68 to an internal controller 76 (FIG. 4), which is implanted in another area of the subject, such as in the subject's abdomen.

Figure 2:
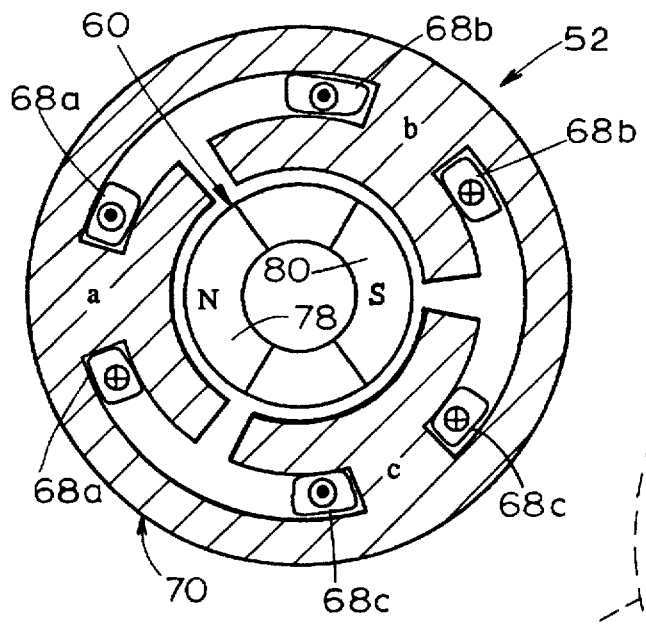
FIG. 2 is a cross sectional view of a simplified DC brushless motor for use in the artificial heart of FIG. 1.
Figure 3:
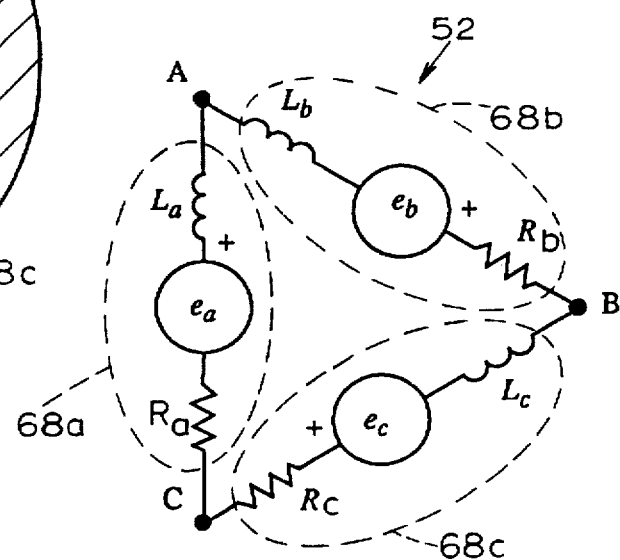
FIG. 3 is an electrical schematic of the motor of FIG. 2.

FIG. 2 is a cross sectional view of the motor 52 shown in simplified form. The rotor 60 has a pair of permanent magnets 78, 80 disposed thereon, and the stator 70 is provided with a respective winding 68a–68c for each of three phases a, b, c. Although the motor 52 shown in FIG. 2 has two rotor magnets 78, 80 and three windings 68, a more preferable motor would be a 14-pole motor (14 rotor magnets) having 21 windings distributed in 15 slots. FIG. 3 is an electrical schematic diagram illustrating that the windings 68a–68c are delta-connected.

Artificial Heart Electronics

Figure 4:
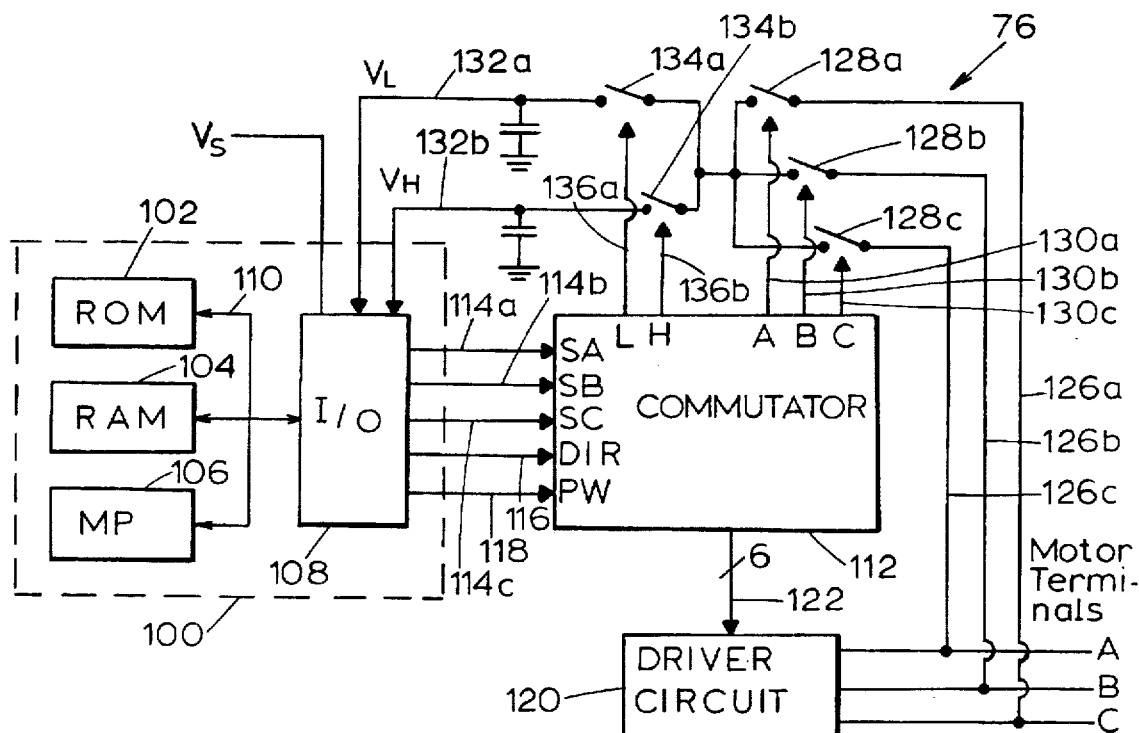
FIG. 4 is a block diagram of the electronics portion of the artificial heart of FIG. 1.

Referring to FIG. 4, the internal controller 76 includes an electronic controller 100, which may be a conventional integrated circuit chip such as an Intel 8XC196KD-20, has a read-only memory (ROM) 102, a random-access memory (RAM) 104, a microprocessor 106, and a conventional input/output (I/O) circuit 108, all of which are interconnected via an address and data bus 110.

Figure 5:
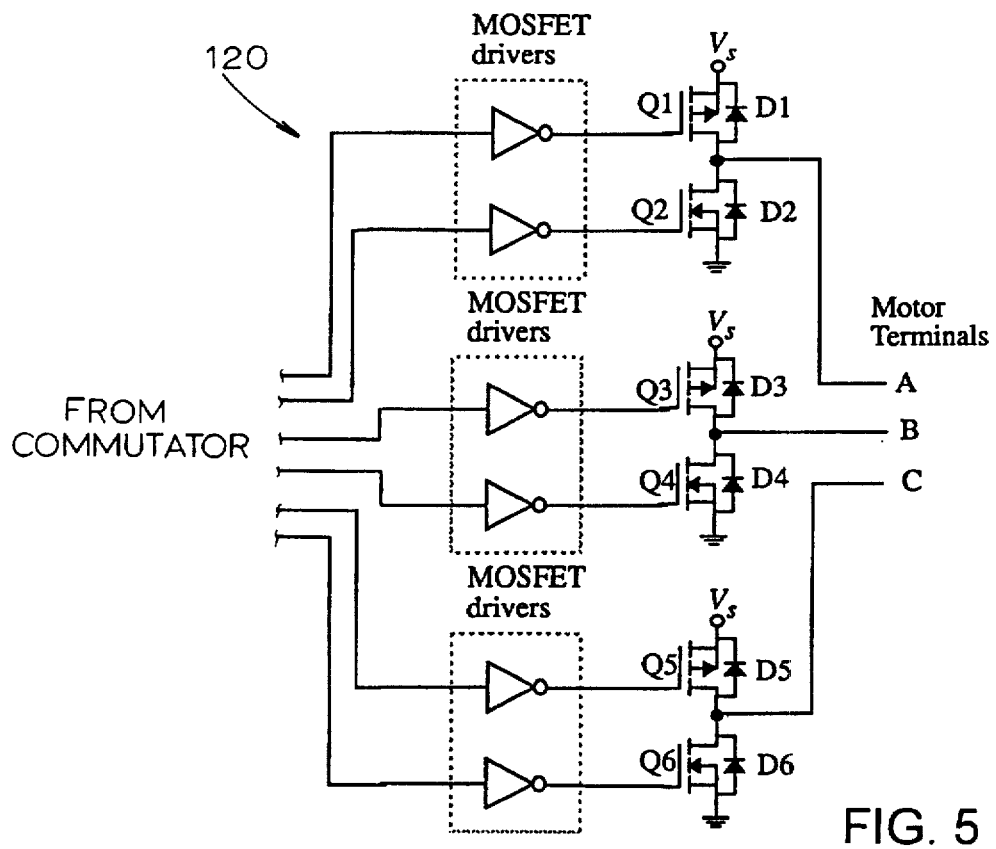
FIG. 5 is a circuit diagram of the driver circuit shown schematically in FIG. 4.

The controller 100 is powered via a battery power source $V_s$ connected to the I/O circuit 108. A commutator circuit 112 is connected to the I/O circuit 108 via three phase-select lines 114a, 114b, 114c, a direction line 116, and a pulse-width control line 118. In response to electrical signals generated on the lines 114–118, the commutator 112 generates six commutation signals and transmits them to a driver circuit 120 via lines 122, which generates and transmits a set of excitation signals to the motor terminals A, B, C. A circuit diagram of the driver circuit 120 is illustrated in FIG. 5.

Three voltage-sensing lines 126a–126c are connected to selectively sense the voltages on the three motor terminals A, B, C (each motor terminal being electrically connected to the windings of two of the three delta-connected phases a, b, c). Each sensing line 126a–126c is coupled to a respective line-select switch 128a–128c, each of which is controlled by a respective line 130a–130c. The lines 126a–126c are connected to a pair of lines 132a, 132b which are connected to the I/O circuit 108 through a pair of line-select switches 134a, 134b which are controlled by a pair of lines 136a, 136b.

FIGS. 6A and 6B illustrate a pair of energization tables for driving the rotor 60, one for clockwise rotation and the other for counterclockwise rotation, for each of six sectors (each of which corresponds to a respective segment of angular position of the rotor 60) through which the rotor 60 can be driven. Referring to FIGS. 6A and 6B, a plus sign (+) indicates that a constant high voltage is supplied to the motor terminal (e.g. by causing Q1 in FIG. 5 to be conductive and Q2 to be nonconductive), a minus sign (−) indicates that the motor terminal is pulse-width modulated (e.g. by repeatedly switching Q1 and Q2 between conductive and nonconductive states), and a blank indicates that the motor terminal is unenergized, and thus has a "floating" voltage (in this case, both Q1 and Q2 would be nonconductive).

FIG. 7 illustrates the voltage sensed on one of the motor terminals for a number of angular position sectors. In Sector A the motor terminal has a relatively constant supply voltage $V_s$, in Sectors B and E the motor terminal has a variable floating voltage, and in Sectors C and D the motor terminal has a voltage which is switched, or pulse-width modulated, between $V_s$ and ground.

Overall Operation

Figure 9:
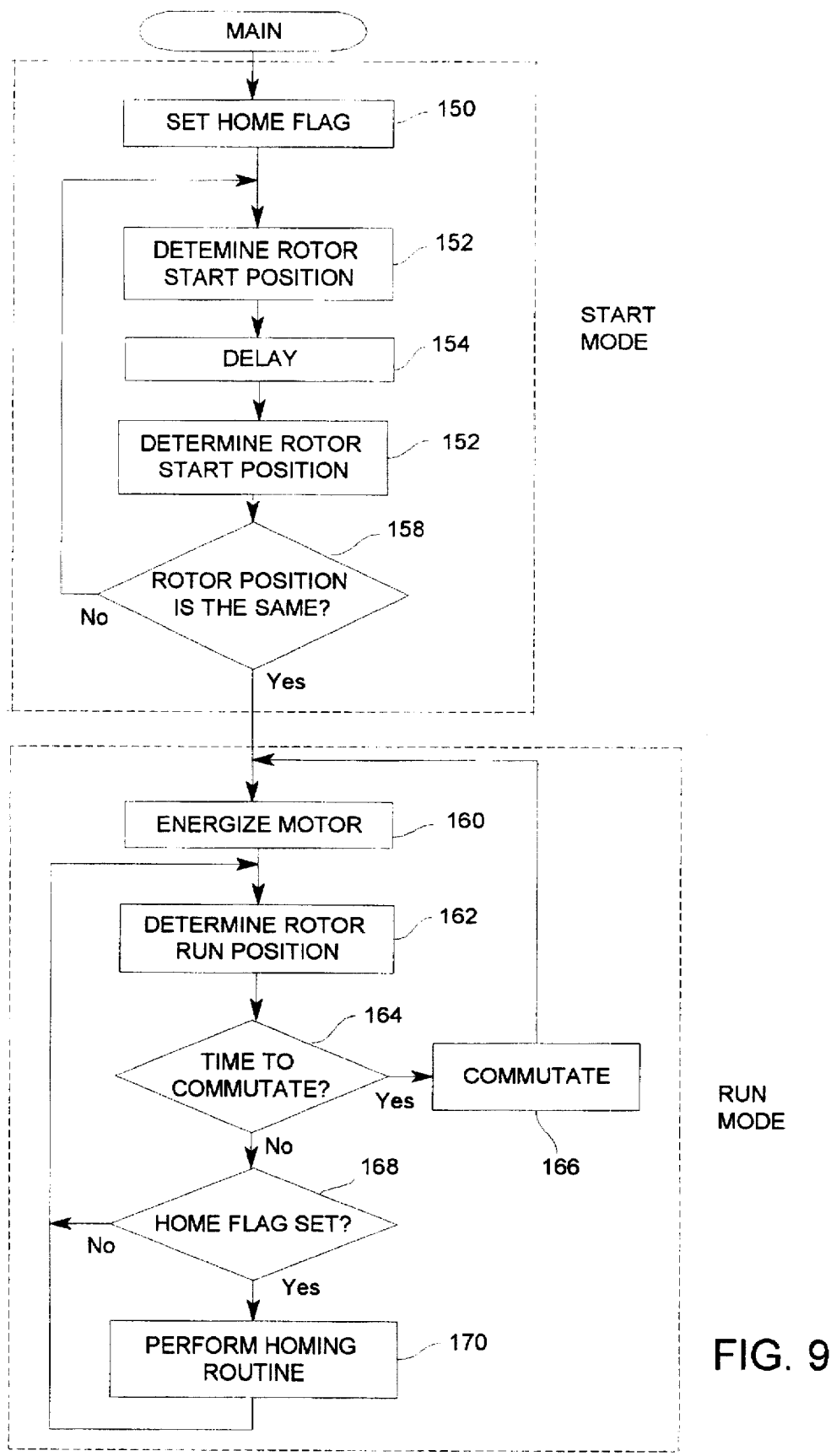
FIG. 9 is a flowchart of the overall operation of the artificial heart.

FIG. 9 is a flowchart of a computer program, stored in the ROM 102 (FIG. 4) and executed by the microprocessor 106, that controls the operation of the artificial heart 10. The basic function of the computer program is to cause the motor 52 to reciprocate the drive screw 54 and the attached pusher plates 30, 50 back and forth, at a rate corresponding to that of the subject's heartbeat (in excess of 30 times per minute), so that blood is pumped through the artificial heart 10 along the flow pathways described above.

Referring to FIG. 9, the computer program has two basic operating modes, a start mode and a run mode. The start mode is performed once just after the artificial heart 10 is implanted into the subject and is not normally performed thereafter (except in cases of emergency, for example, when the heart 10 is "reset"). During the start mode, the rotor 60 is stationary and does not move relative to the stator 70.

At step 150, a home variable or flag is set (e.g. set equal to one) to indicate that a homing routine should be subsequently performed. The angular position of the rotor 60, i.e. which of the six angular position sectors (FIGS. 6A and 6B) the rotor 60 is in with respect to the stator 70, is determined via a routine 152 described below. After a short delay at step 154, the angular position of the rotor 60 is determined a second time via the routine 152. If the rotor 60 is in the same angular position sector as determined by both performances of the routine 152, it is assumed that the rotor 60 is not moving and that that position sector determined by the routine 152 is the correct sector. If the position sector is not the same, the program branches back to perform the routine 152 again.

When the rotor position has been correctly determined, the program branches to step 160 of the run mode where the stator windings 68 are energized, based on the rotor position determined by the routine 152, to cause the rotor 60 to move relative to the stator 70. The very first time that the stator windings 68 are energized at step 160, the rotor 60 is excited in the counterclockwise direction to cause the drive screw 54 and the pusher plates 30, 50 to move leftward in FIG. 1 since the home position is defined to be the leftmost position to which the pusher plates 30, 50 can be moved.

The position of the rotor 60, which is now moving relative to the stator 70, is then determined via a routine 162 described below. At step 164, if the rotor position has changed to a new sector, then the program branches to step 166 where the rotor 60 is commutated by sending a new set of excitation signals to the windings 68 corresponding to the new sector.

At step 168, if the home flag is set, then the program branches to step 170 where a homing routine is performed to cause the rotor 60 to drive the pusher plates 30, 50 to a predetermined home position. The homing routine is normally performed only once, when the artificial heart 10 is first turned on after being implanted.

Determination of Initial Rotor Position

The angular position of the rotor 60 with respect to the stator 70 is determined based upon the phase inductances generated in the stator 70 due to the angular position of the rotor 60. Referring to the top portion of FIG. 10, the phase inductances $L_a$, $L_b$, $L_c$ in the three motor phases a, b, c are shown to vary with the angular position of the rotor 60 relative to the stator 70. However, a phase inductance cannot be measured independently of the others since the windings 68 are delta-connected.

It has been determined that the ratio of two of the three phase inductances of the windings 68 is indicative of rotor position. Referring to FIG. 3, if an excitation voltage $V_s$ is applied across terminals A and C at a relatively high frequency (thus causing the magnitudes of the inductive reactances $L_b$ and $L_c$ to dominate over the resistances $R_b$ and $R_c$), then the magnitude of the voltage $V_u$ on the unenergized motor terminal B (i.e. the voltage across terminals B and C, which is determined by voltage division) is in accordance with the following equation (assuming the rotor 60 is not moving and the DC current in the stator 70 is zero):

$$V_u = [L_c/(L_b+L_c)]V_s$$

The above equation can be generalized in accordance with the following equation:

$$V_u = \alpha_{xy} V_s,$$

where the inductance ratio $\alpha_{xy}$ is equal to $L_y/(L_x+L_y)$, where $L_x$ and $L_y$ are the inductances of motor phases x and y, respectively, where the first subscript x of $\alpha_{xy}$ represents the upper motor phase of the voltage divider (the phase connected to $V_s$) and where the second subscript y of $\alpha_{xy}$ represents the lower motor phase of the voltage divider (the phase connected to ground).

Figure 10:
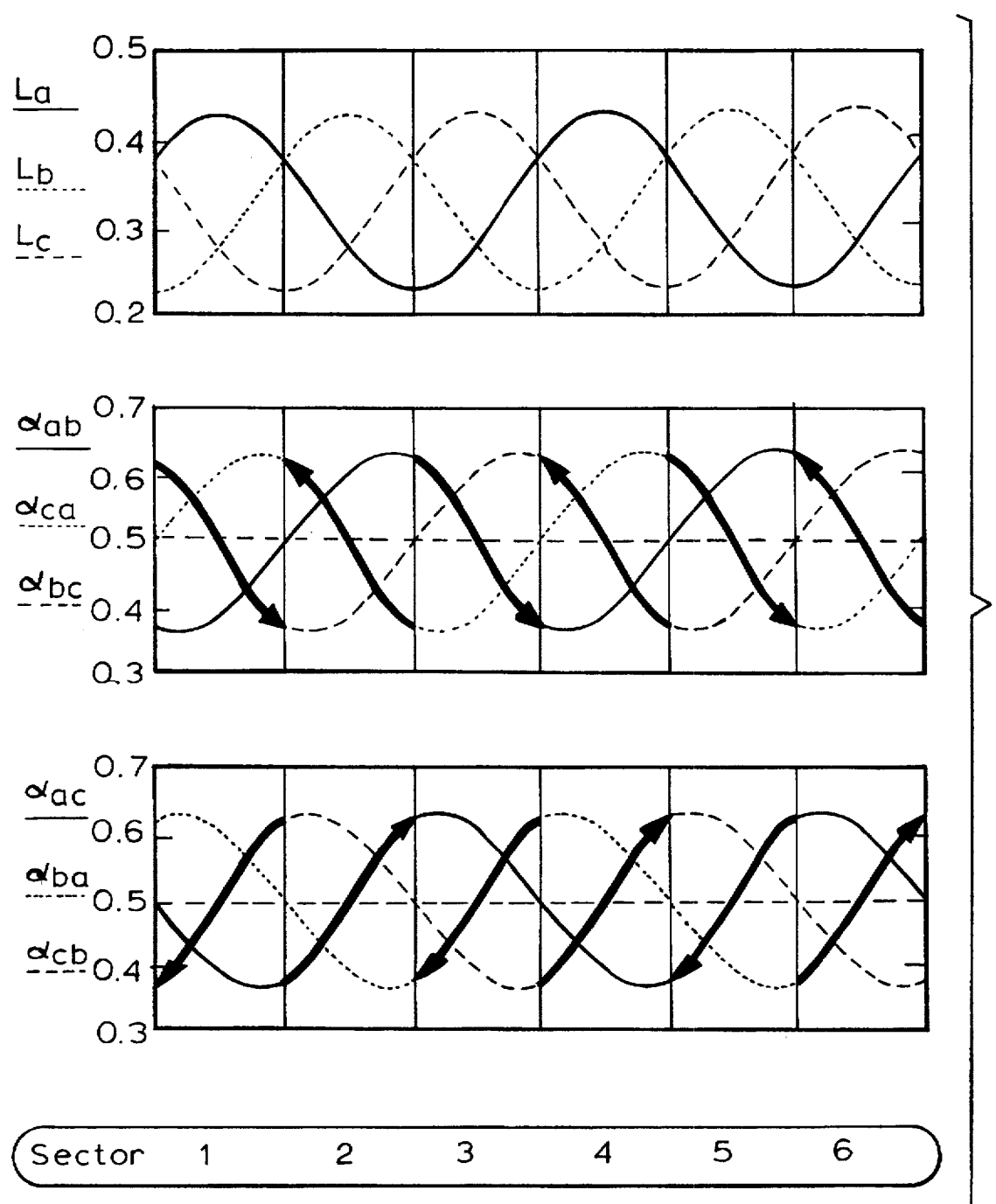

Graphs of the inductance ratios for a motor having three phases a, b, c are shown in the middle and lower portions of FIG. 10 relative to the angular position of the rotor 60. The portions of the inductance ratio curves shown in bold are those portions of the curves which can be determined by sensing the voltage at the unenergized motor terminal. The arrowheads shown on the bold portions of the inductance ratio curves indicate direction of rotation, leftwardly pointing arrows corresponding to clockwise rotor rotation and rightwardly pointing arrows corresponding to counterclockwise rotor rotation.

When a pair of motor terminals are excited with a pulse-width modulated excitation signal, the voltage $V_u$ on the unenergized motor terminal oscillates between a relatively high value $V_H$ and a relatively low value $V_L$, as shown in sectors B and E of FIG. 7 and FIG. 8, which is a simplified illustration of a portion of the voltage waveform in Sector B of FIG. 7.

Figure 13:
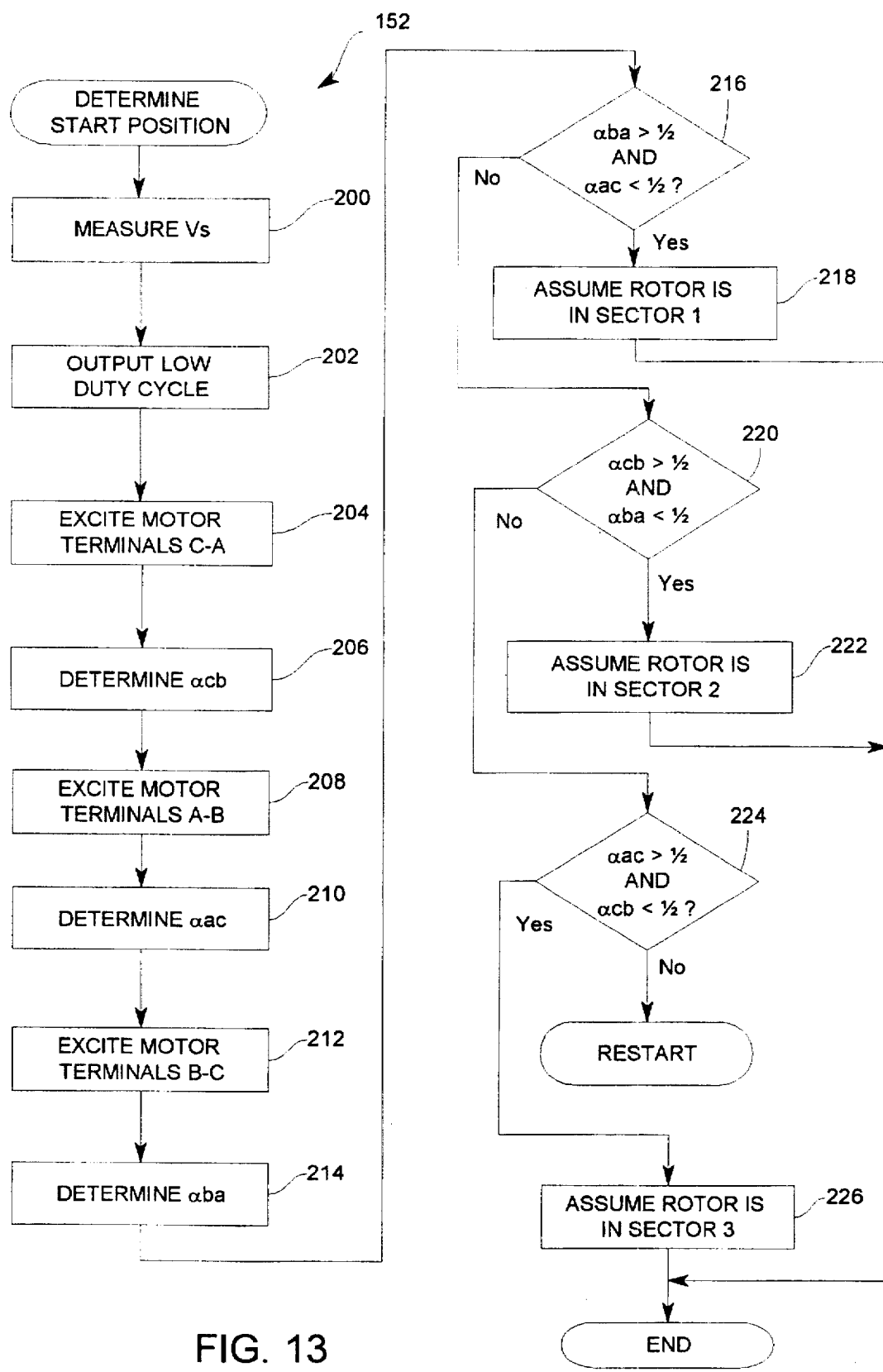
FIG. 13 is a flowchart of a determine start position routine shown schematically in FIG. 9.

FIG. 13 is a flowchart of the routine 152 that determines which position sector that the rotor 60 is in when the rotor 60 is stationary, before the artificial heart 10 begins pumping. Referring to FIG. 13, at step 200 the supply voltage $V_s$ is measured by the I/O circuit 108 via an internal A/D converter (not shown). At step 202, a signal is transmitted to the commutator 112 via the line 118 to set the duty cycle of the pulse-width modulated signals to be supplied to the stator windings 68 to a relatively low value, e.g. 20% duty cycle, so that the rotor 60 is not caused to move.

At step 204, the motor terminals C, A are excited with the excitation signals generated by the driver circuit 120 under the control of the commutator 112 for a short duration of approximately 220 microseconds. The direction specified by the direction line 116 in FIG. 4 does not matter at this point since the duty cycle of the excitation signals and the duration of application are too low to cause the rotor 60 to move.

At step 206, the inductance ratio $\alpha_{cb}$ is determined by measuring the voltage $V_L$ on the unenergized motor terminal B, and then dividing the magnitude of that voltage $V_L$ by the magnitude of the supply voltage $V_s$ measured at step 200. To measure the voltage $V_L$, the commutator 112 closes the switch 128b and opens the switches 128a, 128c via the control lines 130a–130c and causes the switch 134a to be closed only during the $V_L$ portion of the waveform $V_u$ of FIG. 8.

At step 208, the motor terminals A, B are excited (terminal A with positive polarity and terminal B with negative polarity), and at step 210 the inductance ratio $\alpha_{ac}$ is determined by measuring the voltage $V_L$ on the unenergized motor terminal C and dividing the magnitude of that voltage $V_L$ by the magnitude of the supply voltage $V_s$. At step 212, the motor terminals B, C are excited, and at step 214 the inductance ratio $\alpha_{ba}$ is determined by measuring the voltage $V_L$ on the unenergized motor terminal A and dividing the magnitude of that voltage $V_L$ by the magnitude of the supply voltage $V_s$.

At step 216, if the inductance ratio $\alpha_{ba}$ is greater than ½ and if the inductance ratio $\alpha_{ac}$ is less than ½, then the program branches to step 218 where it is (arbitrarily) assumed that the rotor 60 is in Sector 1. The determination made at step 216 is based on the magnitudes of the inductance ratios as set forth in FIG. 10. Referring to the lower portion of FIG. 10, it can be seen that the only sectors in which $\alpha_{ba}$ is always greater than ½ and $\alpha_{ac}$ is always less than ½ are Sectors 1 and 4. Consequently, in that case, the rotor 60 may be in either Sector 1 or Sector 4. The assumption at step 218 that the rotor 60 is in Sector 1 is later tested to determine whether it is correct.

At step 220, if the inductance ratio $\alpha_{cb}$ is greater than ½ and if the inductance ratio $\alpha_{ba}$ is less than ½, then the program branches to step 222 where it is assumed that the rotor 60 is in Sector 2. Referring to the lower portion of FIG. 10, it can be seen that the only sectors in which $\alpha_{cb}$ is always greater than ½ and $\alpha_{ba}$ is always less than ½ are Sectors 2 and 5. The assumption at step 222 that the rotor 60 is in Sector 2 is later tested to determine whether it is correct.

At step 224, if the inductance ratio $\alpha_{ac}$ is greater than ½ and if the inductance ratio $\alpha_{cb}$ is less than ½, then the program branches to step 226 where it is assumed that the rotor 60 is in Sector 3. Referring to the lower portion of FIG. 10, it can be seen that the only sectors in which $\alpha_{ac}$ is always greater than ½ and $\alpha_{cb}$ is always less than ½ are Sectors 3 and 6. The assumption at step 226 that the rotor 60 is in Sector 3 is later tested to determine whether it is correct.

During normal operation, one of the tests of steps 216, 220, 224 will be satisfied. However, in the event none are satisfied, the program branches from step 224 to a restart mode, in which the operation of the artificial heart 10 is restarted.

Determination of Moving Rotor Position

The time at which the rotor 60 moves from one angular position sector to the next angular position sector can also be determined by sensing the voltage at the unenergized motor terminal. When the rotor 60 reaches the new angular position sector, a new set of commutation signals is sent by the commutator 112 to the driver circuit 120 via the lines 122.

Referring to FIG. 11A, the inductance ratios discussed above vary from a maximum value $\alpha_H$ to a minimum value $\alpha_L$ over the six angular position sectors. FIG. 11A is constructed from the bold inductance ratio curves shown in FIG. 10 by combining the counterclockwise curve portions (the portions with arrows pointing left to right) into a single curve while maintaining the bold portions within their original sectors.

The magnitudes (ignoring the oscillations of the pulse width modulated signals) of the voltages $V_H$ and $V_L$ at the unenergized motor terminal are shown in FIG. 11B. The crosshatched portion in FIG. 11B represents the area in which the upper half of the $V_H$ signal is clipped (and therefore unusable) due to the diodes of the driver circuit 120. The $V_L$ voltage periodically reaches a threshold value $T_2$.

A graph of the voltage difference $\Delta V$ between the $V_H$ and $V_L$ voltages is shown in FIG. 11C. The cross-hatched area of FIG. 11C represents the portion of the $\Delta V$ signal that is unusable due to the clipping (in FIG. 11B) of the upper portion of the $V_H$ signal. As shown in FIG. 11C, the $\Delta V$ signal periodically reaches a threshold value $T_1$.

It can be seen that the precise time at which the rotor 60 moves from Sector 1 to Sector 2, from Sector 3 to Sector 4, and from Sector 5 to Sector 6 can be determined by detecting when the $\Delta V$ signal shown in FIG. 11C reaches the $T_1$ threshold. It should also be noted that the precise time at which the rotor 60 moves from Sector 2 to Sector 3, from Sector 4 to Sector 5, and from Sector 6 to Sector 1 can be determined by detecting when the $V_L$ signal shown in FIG. 11B reaches the $T_2$ threshold.

FIGS. 11A–11C are used to determine the sector transition times when the rotor 60 is energized in the counterclockwise direction. FIGS. 12A–12C are used to determine the sector transition times, in the same manner described above, when the rotor 60 is energized in the clockwise direction.

Figure 14:
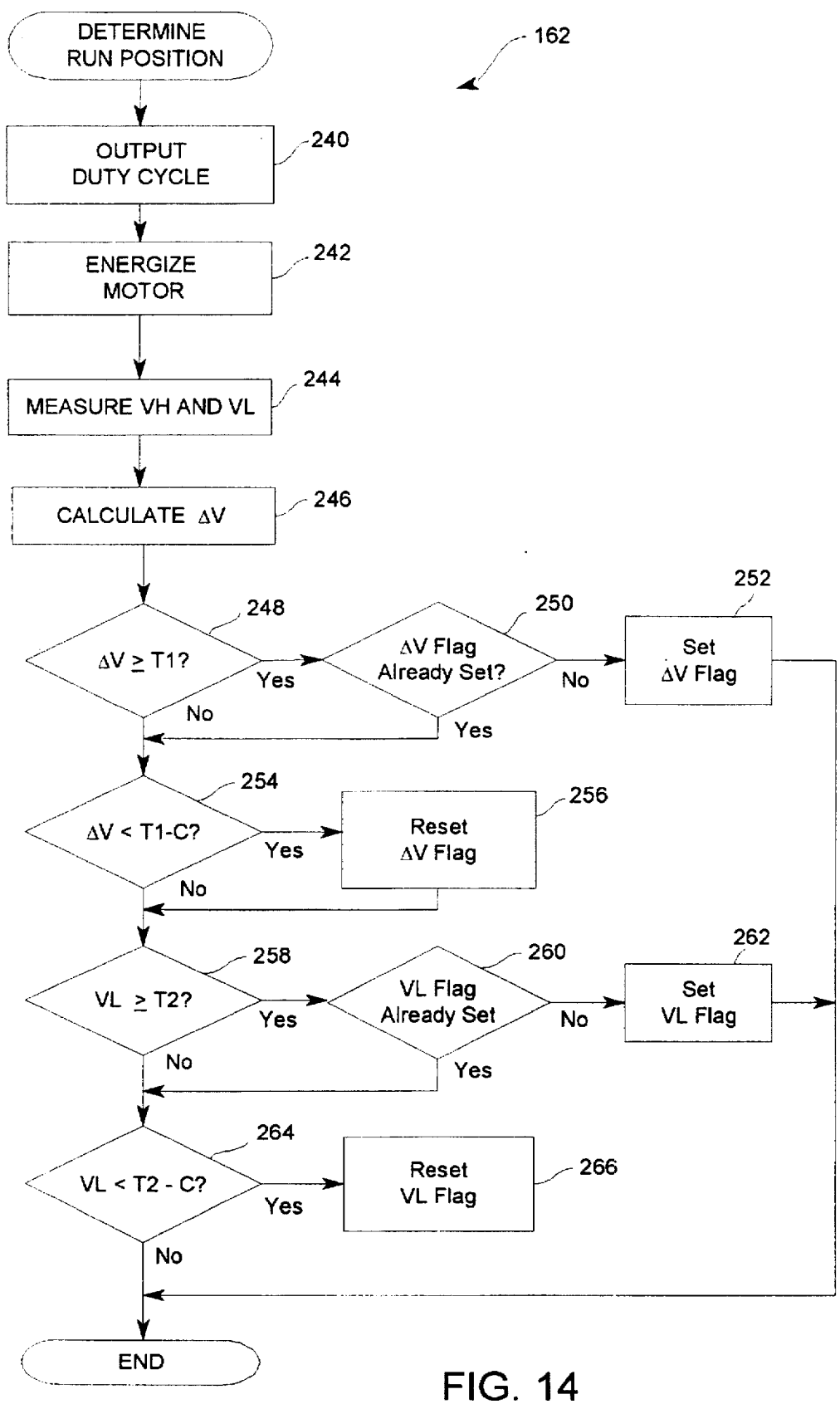
FIG. 14 is a flowchart of a determine run position routine shown schematically in FIG. 9.

FIG. 14 is a flowchart of the routine 162 which is periodically performed at a relatively high rate, such as at least about five times per sector transition, to determine when the rotor 60 reaches a new angular position sector so that a new set of commutation signals can be sent by the commutator 112 to the driver circuit 120 via the lines 122.

At step 240, the duty cycle of the pulse-width modulated commutation signals generated by the commutator 112 is specified via the line 118 (FIG. 4) to the commutator 112. At step 242, a set of commutation signals are transmitted to the driver circuit 120 via the lines 122 (for the duration of the current sector), the commutation signals being based on the desired direction and the current sector (see FIGS. 6A and 6B). Based on the commutation signals, the driver circuit 120 transmits the excitation signals to the motor terminals.

At step 244, the magnitudes of $V_H$ and $V_L$ are measured by closing the switch 128 for the unenergized motor terminal and by toggling the switches 134a, 134b at a rate equal to the rate of the pulse-width modulation so that the $V_H$ signal is always supplied to the I/O circuit 108 (and A/D converter) via the line 132b and so that the $V_L$ signal is always supplied to the I/O circuit 108 (and A/D converter) via the line 132a.

At step 246, the $\Delta V$ signal magnitude is calculated by subtracting the magnitude of the $V_L$ signal magnitude from the $V_H$ signal magnitude. At step 248, if the magnitude of the $\Delta V$ signal is equal to or greater than the threshold $T_1$, then the rotor 60 is entering a new position sector (e.g. moving from Sector 1 to Sector 2, from Sector 3 to Sector 4, or from Sector 5 to Sector 6-see FIG. 11C).

At step 250, if a $\Delta V$ flag has not already been set (e.g. set to equal one), then the program branches to step 252 where the $\Delta V$ flag is set, indicating that it is time for a new set of commutation signals since the rotor 60 has just entered a new angular position sector. If the $\Delta V$ flag was already set (meaning that the routine 162 had already determined, during a recent execution, that the rotor 60 had entered the new sector), then the program branches to step 254, where the magnitude of the $\Delta V$ signal is compared with the threshold $T_1$ minus a small constant value C. If that is the case, meaning that magnitude of the $\Delta V$ signal has decreased from its maximum value, then the $\Delta V$ flag is reset (e.g. reset to zero).

Steps 254 and 256 prevent the routine 162 from erroneously determining that multiple sector transitions are made (due to the fact that $\Delta V$ may surpass the $T_1$ threshold on multiple occasions during successive performances of the routine 162), when in fact only one sector transition is made.

At step 258, if the magnitude of the $V_L$ signal is equal to or greater than the threshold $T_2$, then the rotor 60 is entering a new position sector (e.g. moving from Sector 2 to Sector 3, from Sector 4 to Sector 5, or from Sector 6 to Sector 1-see FIG. 11B).

At step 260, if a $V_L$ flag has not already been set, then the program branches to step 262 where the $V_L$ flag is set, indicating that it is time for a new set of commutation signals since the rotor 60 has just entered a new sector. If the $V_L$ flag was already set (meaning that the routine 162 had already determined, during a recent execution, that the rotor 60 had entered the new sector), then the program branches to step 264, where the magnitude of the $V_L$ signal is compared with the threshold $T_2$ minus a small constant value C. If that is the case, meaning that magnitude of the $V_L$ signal has decreased from its maximum value, then the $V_L$ flag is reset. Steps 264 and 266 are similar to steps 254 and 256 and prevent the routine 162 from erroneously determining that multiple sector transitions are made.

Commutation Routine

Figure 15:
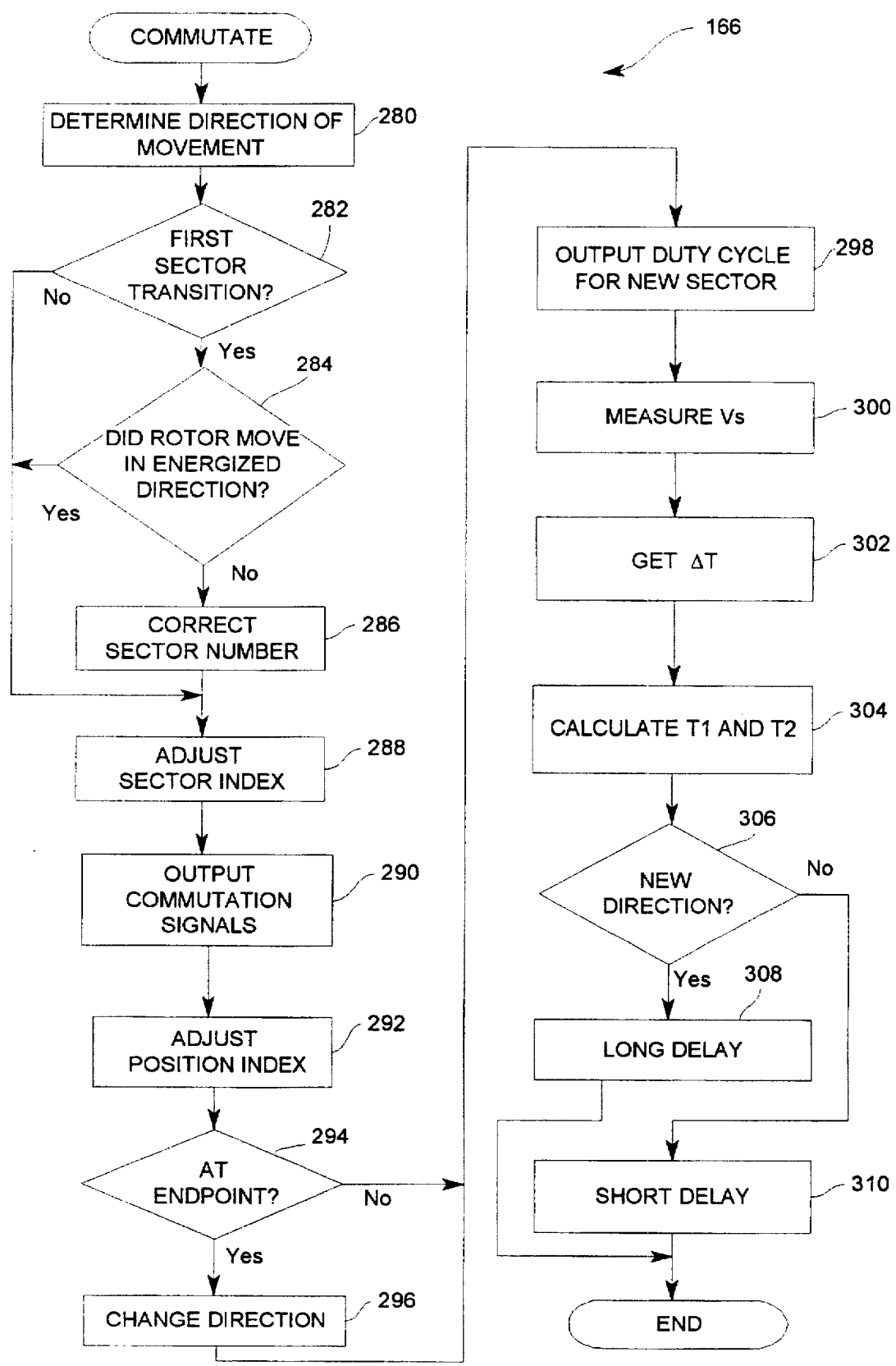
FIG. 15 is a flowchart of a commutate routine shown schematically in FIG. 9.

FIG. 15 is a flowchart of the commutation routine 166 shown schematically in FIG. 9. The commutation routine 166 is performed once each time the rotor 60 enters a new angular position sector, which is determined at step 164 of FIG. 9 by determining if either of the $\Delta V$ or $V_L$ flags were set during the last performance of the routine 162.

Referring to FIG. 15, at step 280, the program determines the direction of actual rotor movement utilizing the table set forth below, based upon the current sector number, which flag was set at one of steps 252, 262, and whether the current excitation of the stator windings 68 corresponds to clockwise or counterclockwise torque (the direction of actual rotor movement may not correspond to the excitation signals provided to the stator windings 68, for example, where a large resistance is encountered).

| SECTOR | FLAG SET | DIRECTION OF ACTUAL ROTOR MOVEMENT | |
|---|---|---|---|
| | | CCW EXCITATION | CW EXCITATION |
| 1,3,5 | $\Delta V$ | CCW | CW |
| 1,3,5 | $V_L$ | CW | CCW |
| 2,4,6 | $\Delta V$ | CW | CCW |
| 2,4,6 | $V_L$ | CCW | CW |

At step 282, if the sector transition was the first transition since the artificial heart 10 was turned on, then the program branches to step 284, where the direction in which the rotor 60 moved as determined in step 280 is compared with the direction for which the excitation signals were generated. If the actual direction of rotor movement is not the same as the intended direction, then the assumption concerning the initial sector position made at one of steps 218, 222, 226 is erroneous, and the sector number is corrected at step 286 by adding three to the initially assumed sector number.

At step 288, the sector number is adjusted by incrementing it if the rotor 60 moved counterclockwise (as determined at step 280) or by decrementing it if the rotor 60 moved clockwise. At step 290, a new set of commutation signals is transmitted from the I/O circuit 108 to the commutator 112 via the lines 114a-114c so that the stator windings 68 will be excited in accordance with the new sector number (the commutation signals are derived from the energization tables shown in FIGS. 6A and 6B as described above).

At step 292, if the sector number has changed from Sector 6 to Sector 1 (with the rotor 60 moving in the counterclockwise direction), or from Sector 1 to Sector 6 (with the rotor 60 moving in the clockwise direction), a position index is adjusted by either incrementing it (if the rotor 60 is moving clockwise) or decrementing it (if the rotor 60 is moving counterclockwise).

At step 294, if the value of the position index has reached one of two endpoint limits, for example if the position index equals zero (corresponding to the leftmost position of the drive screw 54 in FIG. 1) or a predetermined upper value (corresponding to the rightmost position of the drive screw 54), then at step 296, the direction of rotor excitation is changed via the direction line 116 coupled to the commutator 112.

At step 298, the duty cycle of the pulse-width modulated signals sent to the driver circuit 120 is transmitted to the commutator 112 via the line 118. The duty cycle output at step 298 may be recalculated for each new sector using an adaptive feedforward velocity control technique.

At step 300, $V_s$ is measured, and at step 302 the elapsed time $\Delta T$ since the last execution of step 302 (which is approximately equal to the time it took for the rotor 60 to pass through the previous angular position sector) is retrieved from a timer (not shown).

At step 304, the values of the $T_1$ and $T_2$ thresholds are calculated in accordance with the following equations:

$$T_1 = (1-\alpha_L)V_s$$

$$T_2 = \alpha_H V_s + 0.43 K_b \alpha_H (\Delta\theta/\Delta t) - \beta V_s(\alpha_H - \tfrac{1}{2})$$

where $\Delta_L$ and $\Delta_H$ are shown in FIG. 11A, $V_s$ is the supply voltage, $K_b$ is the back-EMF constant of the motor 52, $\Delta\theta$ is the change in angular position of the rotor 60 equal to one sector, $\Delta t$ is the time determined in step 302, and $\beta$ is the duty cycle of the pulse-width modulated excitation signal (equal to $\tau/T$ as shown in FIG. 8).

At step 306, if the rotor 60 is to be moved in a new direction as determined at step 294, then the program branches to step 308 to wait a relatively long time, such as 1840 microseconds, to allow the current in the stator windings 68 to decay. If the rotor 60 is not to be moved in a new direction, the program waits a relatively short time, such as 200 microseconds.

Homing Routine

Figure 16:
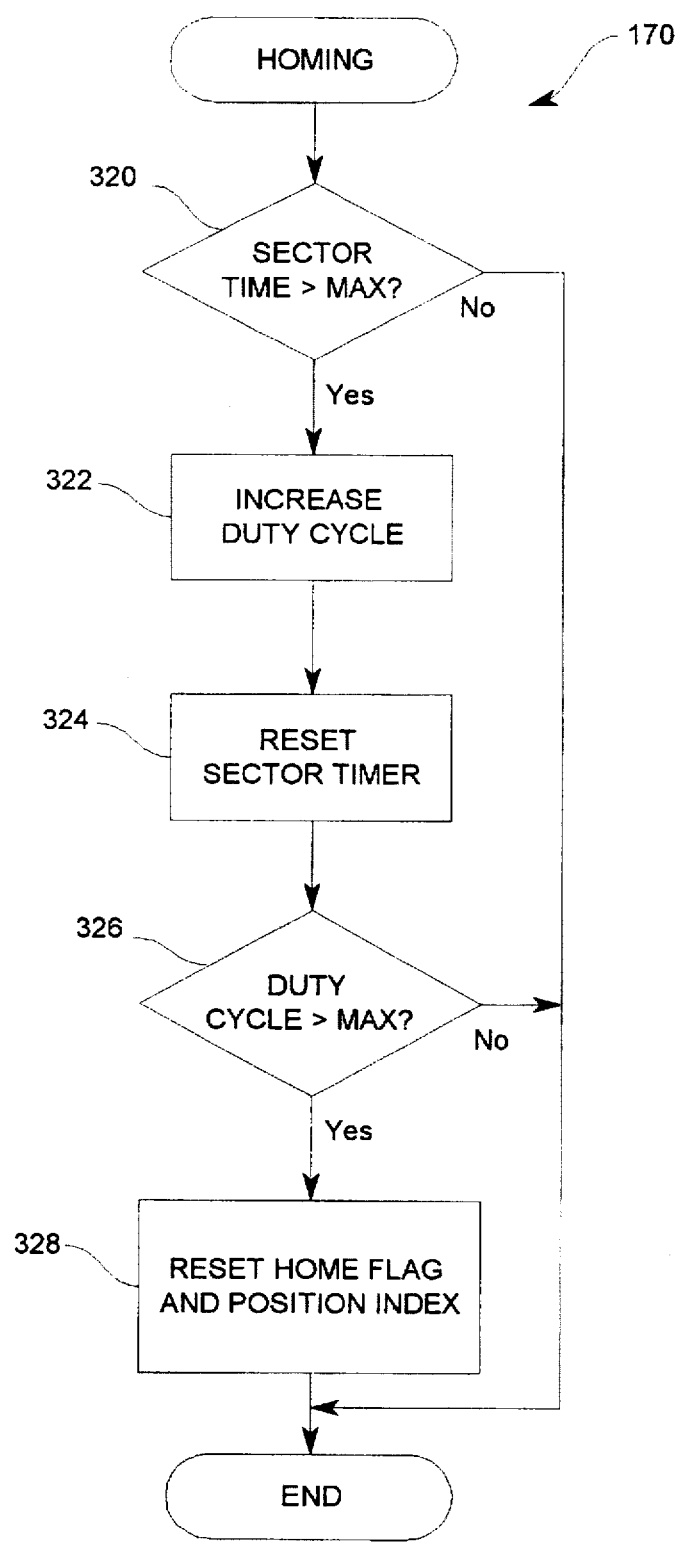
FIG. 16 is a flowchart of a homing routine shown schematically in FIG. 9.

FIG. 16 is a flowchart of the homing routine 170 shown schematically in FIG. 9. Referring to FIG. 16, at step 320, the time in which the rotor 60 has been in the current position sector is compared to determine whether it is greater than a maximum time threshold. If so, then it is assumed that the rotor 60 is no longer moving. At step 322, the duty cycle of the pulse-width modulated commutation signals is increased by a predetermined increment to provide more torque to the motor 52. At step 324, the sector timer (not shown) is reset to zero, and at step 326 the duty cycle of the current excitation signal is compared to determine whether it is greater than a maximum value. If it is, then it is assumed that the drive screw 54 and the pusher plates 30, 50 have reached their right endpoint or home position since the rotor 60 is not moving (the sector time is greater than the maximum as determined at step 320) despite maximum torque (as determined at step 326) being applied to the motor 52.

At step 328, the home flag is reset to zero, and the position index is also set to zero to indicate that the drive screw 54 and pusher plates 30, 50 are at their right endpoint or home position.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. An artificial heart assembly having a sensorless, DC brushless motor, said artificial heart assembly comprising:

a blood inlet conduit;

a blood outlet conduit;

a pumping mechanism for pumping blood from said blood inlet conduit to said blood outlet conduit;

a sensorless, DC brushless motor operatively connected to said pumping mechanism, said motor being reversibly driven in a first direction and a second direction, said motor changing between said first and second directions at a rate of at least 30 times per minute, said motor comprising:

a permanent magnet rotor; and a stator rotatable relative to said permanent magnet rotor, said stator having a plurality of electrically energizable windings and a plurality of motor terminals to which said windings are electrically connected, wherein said rotor may be in Y possible angular position sectors with respect to said stator and wherein Y has a numeric value greater than two;

means for periodically applying electrical signals to a plurality of said motor terminals while leaving at least one of said motor terminals unenergized to cause said rotor to rotate alternately in said first direction and second directions, said rotor changing between said first and second directions at a rate of at least about 30 times per minute;

means for detecting a voltage at said unenergized motor terminal; and means for determining, based upon said voltage detected by said detecting means, that said rotor is in one of X possible angular position sectors, where X has a numeric value less than said numeric value of Y.

2. An artificial heart assembly as defined in claim 1 wherein X has a numeric value not greater than two.

3. An artificial heart assembly as defined in claim 2 wherein Y has a numeric value of at least six.

4. An artificial heart assembly as defined in claim 1 wherein said windings comprise delta-connected windings.

5. An artificial heart assembly as defined in claim 1 wherein said detecting means detects said voltage on said unenergized motor terminal while said rotor is stationary with respect to said stator.

6. An artificial heart assembly as defined in claim 1 wherein said means for applying electrical signals to said motor terminals comprises means for determining when a new set of electrical signals should be applied to said windings, based upon the detection of said voltage at said unenergized motor terminal, in order to move said rotor from a first of said angular position sectors to a second one of said angular position sectors.

7. An artificial heart assembly as defined in claim 1 wherein said means for determining that said rotor is in one of X possible angular position sectors comprises means for determining an inductance ratio based on said voltage on said unenergized terminal.

8. An artificial heart assembly as defined in claim 1 wherein said means for determining that said rotor is in one of X possible angular position sectors comprises means for determining an inductance ratio based on said voltage on said unenergized terminal and comparing said inductance ratio with a threshold value.

9. An artificial heart assembly as defined in claim 1 wherein said means for applying electrical signals to said motor terminals comprises means for applying a voltage across a first pair of said motor terminals during a first period of time while leaving a first motor terminal unenergized, for applying a voltage across a second pair of said motor terminals during a second period of time while leaving a second motor terminal unenergized, and for applying a voltage across a third pair of said motor terminals during a third period of time while leaving a third motor terminal unenergized, and wherein said detecting means comprises means for detecting a first voltage on said first unenergized motor terminal during said first period of time, for detecting a second voltage on said second unenergized motor terminal during said second period of time, and for detecting a third voltage on said third unenergized motor terminal during said third period of time.

10. An artificial heart assembly as defined in claim 9 wherein said means for determining that said rotor is in one of X possible angular position sectors comprises means for determining an inductance ratio based on each of said first, second and third voltages on said unenergized terminals.

11. An artificial heart assembly as defined in claim 9 wherein said means for determining that said rotor is in one of X possible angular position sectors comprises:
   means for determining a first inductance ratio based on one of said first, second and third voltages on said unenergized terminals and a second inductance ratio based on another of said first, second and third voltages on said unenergized terminals; and
   means for comparing said first inductance ratio with a threshold value to determine whether said first inductance ratio is greater than said threshold value and for comparing said second inductance ratio with said threshold value to determine whether said second inductance ratio is less than said threshold value.

12. An artificial heart assembly as defined in claim 1 wherein said determining means determines which of said angular position sectors said rotor is in.

13. An artificial heart assembly as defined in claim 1 additionally comprising a membrane defining a blood chamber fluidly coupled to said blood inlet conduit and said blood outlet conduit, wherein said pumping mechanism comprises a pusher plate which makes contact with said membrane to force blood from said blood inlet conduit to said blood outlet conduit.

14. An artificial heart assembly as defined in claim 1 additionally comprising:
   a first membrane defining a blood chamber fluidly coupled to said blood inlet conduit and said blood outlet conduit, wherein said pumping mechanism comprises a pusher plate which makes contact with said first membrane to force blood from said blood inlet conduit to said blood outlet conduit;
   a second membrane defining a second blood chamber fluidly coupled to a second blood inlet conduit and a second blood outlet conduit; and
   a second pusher plate which makes contact with said second membrane to force blood from said second blood inlet conduit to said second blood outlet conduit.

15. An artificial heart assembly having a sensorless, DC brushless motor, said artificial heart assembly comprising:
   a blood inlet conduit;
   a blood outlet conduit;
   a pumping mechanism for pumping blood from said blood inlet conduit to said blood outlet conduit;
   a sensorless, DC brushless motor coupled to said pumping mechanism, said motor comprising:
      a permanent magnet rotor; and
      a stator rotatable relative to said permanent magnet rotor, said stator having a plurality of electrically energizable windings and a plurality of motor terminals to which said windings are electrically connected, said rotor being movable from a first angular position sector relative to said stator to a second angular position sector relative to said startor;
   means for periodically applying electrical signals to a plurality of said motor terminals while leaving at least one of said motor terminals unenergized to produce on said unenergized motor terminal a periodic signal which undergoes a least three cycles while said rotor is one of said angular position sectors and which has a plurality of relatively high voltage portions $V_H$ alternated with a plurality of relatively low voltage portions $V_L$;
   and means for determining when a new set of electrical signals should be applied to said windings, based upon detection of the magnitude of at least one of said voltage portions of said periodic signal on said unenurgized motor terminal, in order to move said rotor from said first angular position sector to said second angular position sector.

16. An artificial heart assembly as defined in claim 15 wherein said means for applying electrical signals applies a pulse-width modulated signal to at least one of said motor terminals and wherein said means for determining when a new set of electrical signals should be applied to said windings comprises means for determining when one of said voltage portions $V_L$ reaches a threshold value.

17. An artificial heart assembly as defined in claim 15 wherein said means for applying electrical signals applies a pulse-width modulated signal to at least one of said motor terminals, additionally comprising means for calculating a voltage difference $\Delta V$ between one of said voltage portions $V_H$ and one of said voltage portions $V_L$, and wherein said determining means determines when a new set of electrical signals should be applied to said windings based upon said voltage difference $\Delta V$.

18. An artificial heart assembly as defined in claim 15 wherein said means for applying electrical signals applies a pulse-width modulated signal to at least one of said motor terminals, additionally comprising means for calculating a voltage difference $\Delta V$ between one of said voltage portions $V_H$ and one of said voltage portions $V_L$, and wherein said means for determining when a new set of electrical signals should be applied to said windings comprises means for determining when said voltage difference $\Delta V$ reaches a threshold value.

19. An artificial heart assembly as defined in claim 15 wherein said rotor may be in Y possible angular position sectors with respect to said stator and wherein Y has a numeric value greater than two, additionally comprising means for determining, based upon said voltage detected by said detecting means, that said rotor is in one of X possible positions, where X has a numeric value less than said numeric value of Y.

20. An artificial heart assembly as defined in claim 15 additionally comprising means for keeping track of the current position of the pumping mechanism.

21. An artificial heart assembly as defined in claim 15 wherein said windings comprise delta-connected windings.

22. An artificial heart assembly as defined in claim 15 additionally comprising a membrane defining a blood chamber fluidly coupled to said blood inlet conduit and said blood outlet conduit, wherein said pumping mechanism comprises a pusher plate which makes contact with said membrane to force blood from said blood inlet conduit to said blood outlet conduit.

23. An apparatus as defined in claim 15 wherein said means for periodically applying electrical signals to said motor terminals comprises means for causing said rotor to change between first and second alternating directions at a rate of at least about 30 times per minute.

24. An artificial heart assembly having a sensorless, DC brushless motor, said artificial heart assembly comprising:
   a blood inlet conduit;
   a blood outlet conduit;
   a pumping mechanism for pumping blood from said blood inlet conduit to said blood outlet conduit;
   a sensorless, DC brushless motor coupled to said pumping mechanism, said motor comprising:

a permanent magnet rotor; and a stator rotatable relative to said permanent magnet rotor, said stator having a plurality of electrically energiziable windings and a plurality of motor terminals to which said windings are electrically connected, said rotor being movable from a first angular position sector relative to said stator to a second angular position sector relative to said stator;

means for periodically applying electrical signals to a plurality of said motor terminals while leaving at least one of said motor terminals unenergized to cause said rotor to rotate alternately in said first direction and second directions, said rotor changing between said first and second directions at a rate of at least about 30 times per minute;

means for periodically detecting a voltage at said unenergized motor terminal; and means for determining when a new set of electrical signals should be applied to said windings, based upon the detection of said voltage at said unenergized motor terminal, in order to move said rotor from said first angular position sector to said second angular position sector, wherein said means for applying electrical signals applies a pulse-width modulated signal to at least one of said motor terminals, wherein said voltage at said unenergized motor terminal has a plurality of relatively high voltage portions $V_H$ alternated with a plurality of relatively low voltage portions $V_L$, and wherein said determining means determines when a new set of electrical signals should be applied to said windings based upon one of said voltage portions $V_L$.

25. An artificial heart assembly having a sensorless, DC brushless motor, said artificial heart assembly comprising:

a blood inlet conduit;

a blood outlet conduit;

a pumping mechanism for pumping blood from said blood inlet conduit to said blood outlet conduit; and a sensorless, DC brushless motor coupled to said pumping mechanism, said motor comprising:

a permanent magnet rotor; and a stator rotatable relative to said permanent magnet rotor, said stator having a plurality of electrically energiziable windings and a plurality of motor terminals to which said windings are electrically connected said rotor being movable from a first angular position sector relative to said stator to a second angular position sector relative to said stator;

means for periodically applying electrical signals to a plurality of said motor terminals while leaving at least one of said motor terminals unenergized to cause said rotor to rotate alternately in said first direction and second directions, said rotor changing between said first and second directions at a rate of at least about 30 times per minute;

means for periodically detecting a voltage at said unenergized motor terminal;

means for determining when a new set of electrical signals should be applied to said windings, based upon the detection of said voltage at said unenergized motor terminal, in order to move said rotor from said first angular position sector to said second angular position sector; and means for keeping track of the current angular position sector occupied by the rotor.

26. An artificial heart assembly having a sensorless, DC brushless motor, said artificial heart assembly comprising:

a blood inlet conduit;

a blood outlet conduit;

a pumping mechanism for pumping blood from said blood inlet conduit to said blood outlet conduit;

a sensorless, DC brushless motor coupled to said pumping mechanism, said motor comprising:

a permanent magnet rotor; and a stator rotatable relative to said permanent magnet rotor, said stator having a plurality of electrically energizable windings and a plurality of motor terminals to which said windings are electrically connected, said rotor being movable from a first angular position sector relative to said stator to a second angular position sector relative to said stator;

means for periodically applying electrical signals to a plurality of said motor terminals while leaving at least one of said motor terminals unenergized to cause said rotor to rotate alternately in said first direction and second directions, said rotor changing between said first and second directions at a rate of at least about 30 times per minute;

means for periodically detecting a voltage at said unenergized motor terminal;

means for determining when a new set of electrical signals should be applied to said windings, based upon the detection of said voltage at said unenergized motor terminal, in order to move said rotor from said first angular position sector to said second angular position sector;

a first membrane defining a blood chamber fluidly coupled to said blood inlet conduit and said blood outlet conduit, wherein said pumping mechanism comprises a pusher plate which makes contact with said first membrane to force blood from said blood inlet conduit to said blood outlet conduit;

a second membrane defining a second blood chamber fluidly coupled to a second blood inlet conduit and a second blood outlet conduit; and a second pusher plate which makes contact with said second membrane to force blood from said second blood inlet conduit to said second blood outlet conduit.

27. A method of operating an artificial heart assembly having a blood inlet conduit, a blood outlet conduit, a pumping mechanism for pumping blood from the blood inlet conduit to the blood outlet conduit, and a sensorless DC brushless motor coupled to the pumping mechanism and having a permanent magnet rotor, a stator rotatable relative to the rotor and having a plurality of electrically energizable windings and a plurality of motor terminals to which the windings are electrically connected, the rotor being movable from a first angular position sector relative to the stator to a second angular position sector relative to the stator, said method comprising the steps of:

(a) periodically applying electrical signals to a plurality of the motor terminals while the rotor is moving relative to the stator and while leaving at least one of the motor terminals unenergized to produce on said unenergized motor terminal a periodic signal which undergoes at least three cycles while said rotor is in one of said angular position sectors and which has a plurality of relatively high voltage portions alternated with a plurality of relatively low voltage portions; and (b) determining when a new set of electrical signals should be applied to the windings, based upon one of said voltage portions of said periodic signal on the unenergized motor terminal, in order to move the rotor from the first angular position sector to the second angular position sector.

28. A method as defined in claim 27 wherein said step (a) comprises the step of periodically applying electrical signals to a plurality of the motor terminals while the rotor is moving relative to the stator to cause the rotor to rotate alternately in the first direction and second directions at a rate of at least about 30 times per minute.

29. A method as defined in claim 27 wherein said step (a) comprises the step of applying a pulse-width modulated signal to at least one of the motor terminals, said method additionally comprising the steps of:

(c1) detecting a plurality of relatively high voltage portions $V_H$ on the unenergized motor terminal; and (c2) detecting a plurality of relatively low voltage portions $V_L$ on the unenergized motor terminal.

30. A method as defined in claim 29 wherein said step (b) comprises the step of determining when a new set of electrical signals should be applied to the windings based upon the magnitude of one of the voltage portions $V_L$.

31. A method as defined in claim 29 wherein said step (b) comprises the step of determining when a new set of electrical signals should be applied to the windings based upon when one of the voltage portions $V_L$ reaches a threshold value.

32. A method as defined in claim 29 additionally comprising the step of calculating a voltage difference $\Delta V$ between one of the voltage portions $V_H$ and one of the voltage portions $V_L$.

33. A method as defined in claim 32 wherein said step (b) comprises the step of determining when a new set of electrical signals should be applied to the windings based upon the voltage difference $\Delta V$.

34. A method as defined in claim 32 wherein said step (b) comprises the step of determining when a new set of electrical signals should be applied to the windings by determining when the voltage difference $\Delta V$ reaches a threshold value.

35. A method as defined in claim 27 additionally comprising the step of keeping track of the current angular position sector occupied by the rotor.

36. A method as defined in claim 27 additionally comprising the step of keeping track of the current position of the pumping mechanism.

37. An artificial heart assembly having a sensorless, DC brushless motor, said artificial heart assembly comprising:

a blood inlet conduit;

a blood outlet conduit;

a pumping mechanism for pumping blood from said blood inlet conduit to said blood outlet conduit;

a sensorless, DC brushless motor coupled to said pumping mechanism, said motor comprising:

a permanent magnet rotor; and a stator rotatable relative to said permanent magnet rotor, said stator having a plurality of electrically energizable windings and a plurality of motor terminals to which said windings are electrically connected, said rotor being movable from a first angular position sector relative to said stator to a second angular position sector relative to said stator;

means for periodically applying, while said rotor is stationary, electrical signals to a plurality of said motor terminals while leaving at least one of said motor terminals unenergized, at least one of said electrical signals comprising a periodic signal;

means for detecting a voltage at said unenergized motor terminal, said voltage at said unenergized motor terminal having a plurality of relatively high voltage portions $V_H$ alternated with a plurality of relatively low voltage portions $V_L$; and means for determining the position of said rotor, while said rotor is stationary, based upon detection of one of said voltage portions at said unenergized motor terminal.

* * * * *